United States Patent
Rosner et al.

(10) Patent No.: US 6,907,103 B2
(45) Date of Patent: Jun. 14, 2005

(54) CAPTURING IMAGES OF MOVING OBJECTS WITH A MOVING ILLUMINATION POINT SOURCE

(75) Inventors: S. Jeffrey Rosner, Palo Alto, CA (US); Nasreen Gazala Chopra, Belmont, CA (US); Ang Shih, San Jose, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 331 days.

(21) Appl. No.: 10/174,737

(22) Filed: Jun. 19, 2002

(65) Prior Publication Data

US 2003/0235269 A1 Dec. 25, 2003

(51) Int. Cl.[7] .............................................. G01N 23/04
(52) U.S. Cl. .............................. 378/62; 378/57; 378/58
(58) Field of Search ............................... 378/21–26, 57, 378/58, 62, 69, 92, 95, 98.6, 114, 115, 124, 134, 146, 195–197; 250/358.1, 360.1; 600/407, 424, 425, 428, 431, 439, 448; 356/601–640; 342/176; 367/7, 11; 73/599–602

(56) References Cited

U.S. PATENT DOCUMENTS

| | | | | |
|---|---|---|---|---|
| 4,340,816 A | * | 7/1982 | Schott | 378/22 |
| 4,349,740 A | * | 9/1982 | Grassmann et al. | 378/25 |
| 4,926,452 A | * | 5/1990 | Baker et al. | 378/22 |
| 5,090,037 A | | 2/1992 | Toth et al. | |
| 5,142,652 A | * | 8/1992 | Reichenberger et al. | 378/136 |
| 5,267,296 A | | 11/1993 | Albert | |
| 5,293,574 A | * | 3/1994 | Roehm et al. | 378/98.2 |
| 5,369,678 A | * | 11/1994 | Chiu et al. | 378/62 |
| 6,183,139 B1 | * | 2/2001 | Solomon et al. | 378/137 |
| 6,195,450 B1 | * | 2/2001 | Qian et al. | 382/130 |
| 6,463,121 B1 | * | 10/2002 | Milnes | 378/62 |
| 6,483,890 B1 | * | 11/2002 | Malamud | 378/22 |

FOREIGN PATENT DOCUMENTS

| | | |
|---|---|---|
| DE | 198 23 450 A1 | 12/1999 |
| EP | 0 567 320 A2 | 10/1993 |
| EP | 0 897 122 A1 | 2/1999 |

* cited by examiner

*Primary Examiner*—Allen C. Ho

(57) ABSTRACT

An imaging system that is capable of capturing images of moving objects as they are moving with minimal blurring by moving a point source of illumination such that the position from which illumination is projected is changed as the object moves to ensure that the position of the image projected onto an imaging plane remains substantially effectively stationary. The position from which illumination is projected functions as a point source of illumination. A image sensor of the imaging system is positioned in the imaging plane and receives illumination projected from the position of the illumination source that passes through the moving object. The image sensor produces electrical signals in response to the received illumination. Because the image of the moving object remains effectively stationary on the image sensor, which is located in the imaging plane, an image of at least a portion of the moving object can be constructed with minimal blurring and without having to halt the object to capture an image of it. Because it is not necessary to halt the object and allow the object to settle before capturing an image of it, the throughput of the imaging system is increased and the captured images are greatly improved.

12 Claims, 3 Drawing Sheets

CAPTURING IMAGES OF MOVING OBJECTS WITH A MOVING ILLUMINATION POINT SOURCE

BACKGROUND OF THE INVENTION

The present invention relates to optical imaging. More particularly, the present invention relates to capturing images of moving objects by moving the point source of illumination generally synchronously with the motion of the object to prevent or minimize blurring of the captured images while, at the same time, increasing the throughput of the imaging process.

In the field of high-speed industrial imaging, it is desirable to maintain objects in motion at constant velocity in order to maximize the throughput of the production line. Imaging techniques in which imaging is performed by transmission of illumination through an object to a detector, such as in x-ray radiography, are commonly referred to as projection imaging techniques. The images captured during imaging are referred to as projection images. The general problem of imaging an object in motion is a result of the time of the exposure and the apparent motion in the focal plane. In general, if an object travels in one dimension at some velocity $V_O$ during a time, $\Delta t$, which corresponds to the exposure time, then the image will be blurred with an effective resolution of $V_O * \Delta t$.

For many situations, if the exposure time is sufficiently short or if the velocity of the object is sufficiently small, an imaging system can perform the required task of imaging the moving object without unacceptable blurring. However, there are a number of cases where shortening the exposure time or reducing the velocity of the object are not adequate solutions to the problem of blurring, particularly in industrial imaging. For example, in many situations the object velocity may be fixed, or the intensity of the illumination provided by the illumination source may be insufficient to allow short exposure times to be used. In addition, the exposure time may be constrained for some reason. Also, there may be a need to move the object at a speed beyond that at which an acceptable amount of blurring could be obtained.

Another way to avoid or minimize blurring is to stop the motion of the object each time an image of the object is to be captured and capture an image, move the object to the next imaging position, stop the object and capture an image of the object at that position, and so on, as the object is moved along the manufacturing line. However, in many situations, it is highly undesirable to start and stop the object during imaging. Starting and stopping the object during imaging generally results in substantial imaging complexity and delay time because the imaging system must wait for the object to settle into each new position in order to image the object with sufficient precision and to avoid blurring. Also, the delay time associated with stopping and starting the object decreases the throughput of the imaging system.

Accordingly, a need exists for an imaging system that can obtain precise images of an object while the object is in motion while minimizing blurring, thereby maximizing imaging throughput.

SUMMARY OF THE INVENTION

The present invention provides an imaging system that is capable of capturing images of a moving object with minimal blurring by moving a point source of illumination such that the position from which illumination is projected is changed as the object moves to ensure that the position of the image projected onto an imaging plane remains substantially effectively stationary. The position from which illumination is projected functions as a point source of illumination. An image sensor of the imaging system is positioned in the imaging plane and receives illumination projected from the position of the illumination source that passes through the moving object. The image sensor produces electrical signals in response to the received illumination. Because the image of the moving object remains effectively stationary on the image sensor, an image of at least a portion of the moving object can be constructed with minimal blurring and without having to halt the moving object to capture an image of it. Furthermore, because it is not necessary to halt the moving object and to allow the object to settle before capturing an image of it, the throughput of the imaging system is increased and the captured images are greatly improved.

In accordance with the preferred embodiment, the point source position is controlled by processing circuitry in such a manner that the position from which the illumination is projected is changed as the object moves to ensure that the motion of the image on the image sensor is minimized during exposure. The illumination source preferably is a scannable x-ray tube that can be addressed to locate the point source in the tube. The moving object is typically an object being inspected as it moves along a production line. The tube can be addressed to select a particular position on the tube that functions as a point source that projects x-rays isotropically such that the moving object falls within this radiation. The useful portion of this radiation is the amount that intercepts the image sensor after passing through the object. This fraction of the radiation defines a roughly pyramidal shape that is generally referred to in the industry as a cone-beam. The processing circuitry controls the addressing of the tube, and thus the position of the point source, and ensures that the point source moves in the direction of motion of the object at an appropriate velocity to cause an image projected onto the image sensor to remain effectively stationary. By moving the point source in this manner, blurring of the captured images is minimized without the need to halt the moving object and to allow the object to settle before capturing an image of it. This, in turn, allows the throughput of the production line to be increased.

These and other features and advantages of the present invention will become apparent from the following description, drawings and claims.

DETAILED DESCRIPTION OF THE PREFERRED EMBODIMENTS

Figure 1:
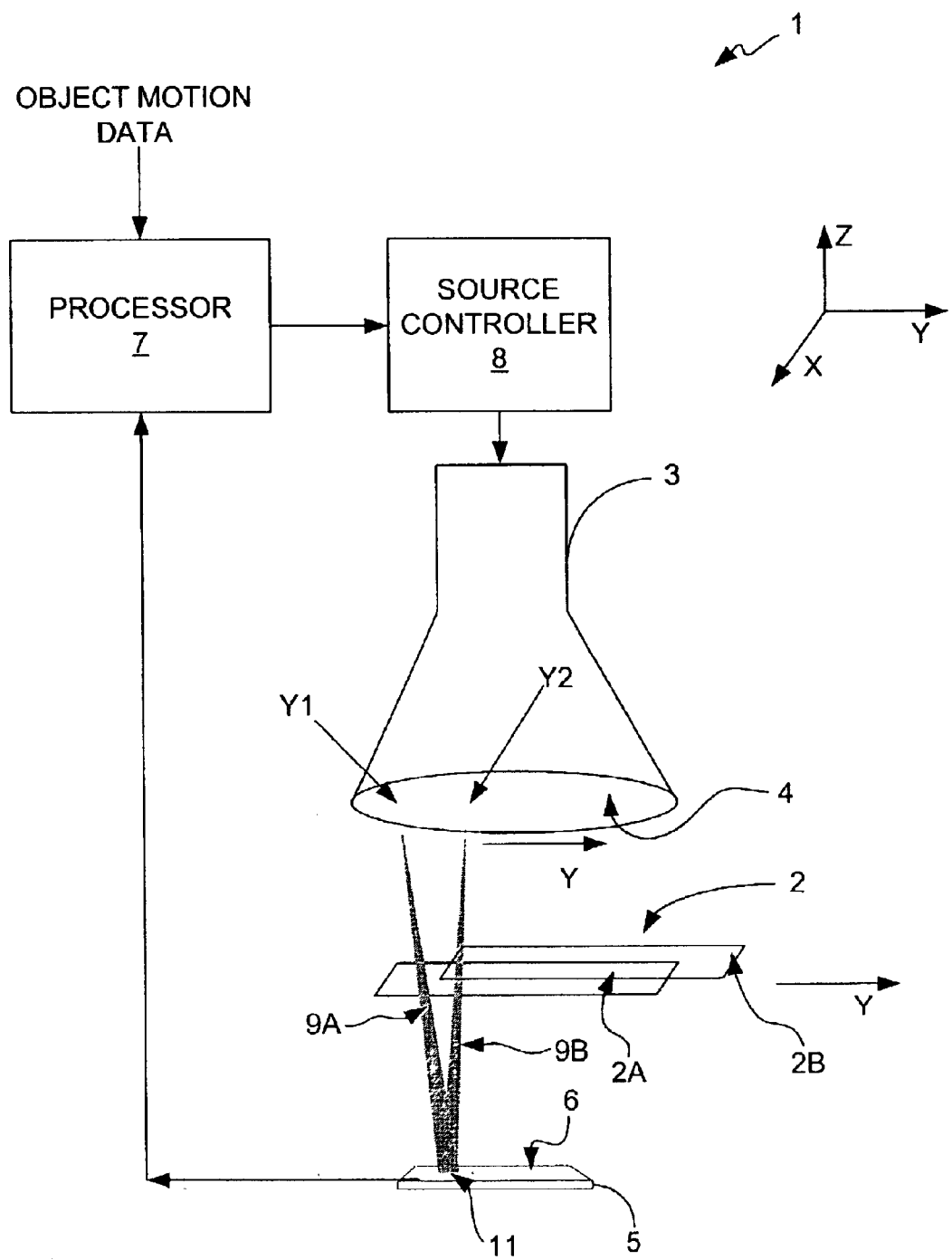
FIG. 1 is a block diagram illustrating an example embodiment of the imaging system of the present invention.

The present invention is directed to projection imaging of an object with a point source of illumination where the location of the point source is addressable, or able to be electrically positioned, in at least one and, in applications in which three-dimensional imaging is performed, in two dimensions. A point source of illumination is defined as a region in space that is comparable to or smaller in dimensions than the imaging resolution desired from the system from which radiation of any form that is used in imaging can be projected. Such radiation can be any radiation that travels in straight lines and interacts with an object, thereby resulting in a change in the nature of the radiation in some form that can represent a property of the object. The radiation could be x-ray radiation, visible light radiation, infrared or ultraviolet radiation, other electromagnetic radiation, such as radio waves or terahertz radiation. The radiation could also be acoustic radiation, for example.

The point source of illumination projects an image of the object onto an image sensor. The point source is moved in the direction of movement of the object and with a velocity that allows radiation from the point source that passes through a given region of the object to be received by a given detector of the image sensor. This enables substantially the same region of the object to be continuously projected onto substantially the same detector of the image sensor during exposure, thereby rendering the object virtually motionless relative to the detector during the imaging process. The point source position is moved in such a manner that the velocity and direction of the point source is generally matched to the velocity and direction of the object.

The present invention is particularly well suited for industrial applications in which relatively flat objects, such as printed circuit boards (PCBs), for example, are moved along a production line as they are imaged with x-rays for the purpose of inspecting the object for defects. Therefore, the invention will be described with respect to this particular application. However, it should be noted that the invention is not limited to this application or to any particular application. The invention is suitable for use in any imaging application where imaging of an object as it moves is necessary or desirable. It should also be noted that the present invention is not limited with respect to the type of source or image sensor employed in the imaging system of the present invention. Also, although the present invention is described with respect to projection imaging, it should be noted that the present invention is applicable to other imaging modalities as well.

In accordance with the present invention, the motion of the object is controlled and tracked. By controlling and tracking the motion of the object, the manner in which the point source of illumination should be moved for a particular imaging plane is determined so that, during exposure, substantially the same region of the object is continuously projected onto the same region of the image sensor. This enables the object to be imaged without motion-induced blurring without having to start and stop the object each time an image of the object is to be captured. In addition to capturing images with minimal blurring, this enables the throughput of the imaging process to be increased. Alternatively, the motion of the object may not be known, but the motion of the object may be tracked to generate tracking data and the appropriate motion of the point source of illumination determined from the tracking data. The manner in which these objectives are achieved in accordance with the present invention will now be described with reference to FIGS. 1, 2 and 4.

Figure 2:
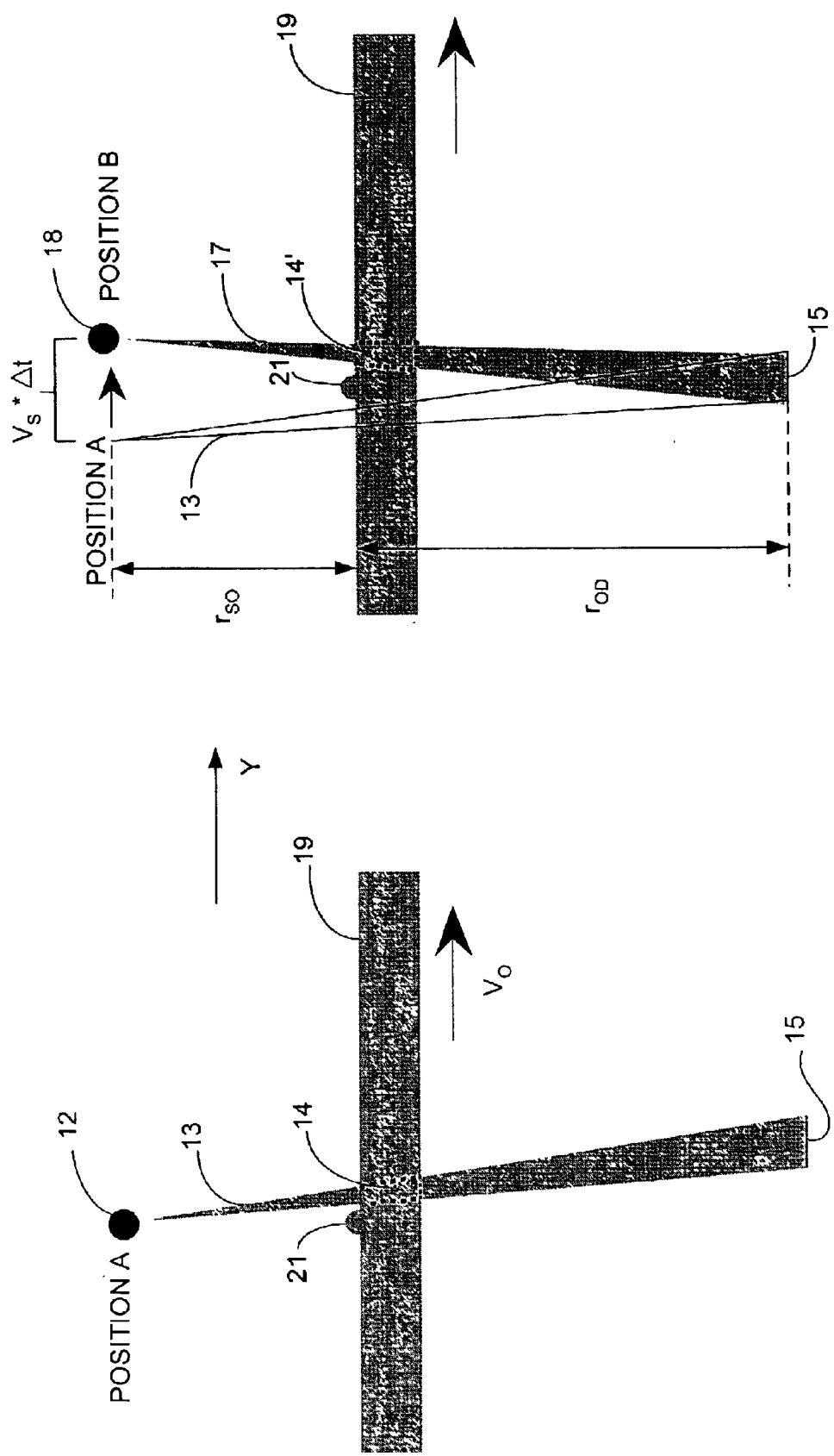
FIGS. 2A and 2B are pictorial representations depicting the manner in which a moving point source illuminates substantially the same region of a moving object when the motion of the point source and of the object are synchronized.

FIG. 1 is a block diagram illustrating the imaging system 1 of the present invention in accordance with an example embodiment. In FIG. 1, the motion of the object 2 being imaged is represented by rectangles 2A and 2B, with rectangle 2A representing a first position of the object as it moves in the Y-direction and rectangle 2B representing a subsequent position of the object 2 as it moves in the Y-direction. As the object 2 moves, it is illuminated with x-rays that are generated by an x-ray source 3, which may be, for example, a scanning x-ray tube with the capability of positioning a point source of illumination on a region of the emitting surface of the tube in an addressable fashion. Scanning x-ray tubes exist that are used for x-ray imaging in medical and industrial applications that are suitable for use with the present invention. An example of a scanning x-ray that is suitable for use with the present invention is the scanning x-ray tube of the Agilent 5DX automated x-ray inspection system.

In the embodiment shown in FIG. 1, the x-ray source 3 is a scanning x-ray tube that is capable of scanning in one or two dimensions. The object 2 shown in FIG. 1 is depicted as moving a single direction, namely, the Y-direction. The object 2 may be imaged with minimal blur while it is moving by addressing the x-ray scanning tube such that the point source moves in the Y-direction at a velocity that corresponds to the velocity of the object 2 in the Y-direction. Because the point source is only moving in the Y-direction, it is not necessary to use an addressable x-ray source that enables the point source to be moved in both the X and Y-directions. Thus, simpler configurations than a two-dimensional (2-D) scanning x-ray tube may be used for the purpose of scanning in the Y-direction. However, it can be advantageous to move the point source in both the X and Y directions, and using a two-dimensional scanning X-ray tube as the scanning x-ray tube 3 allows the point source to be moved in either or both of these directions. This allows 3-D image information to be obtained (i.e., X, Y and Z). Any scanning x-ray tube having a length (Y)-to-width (X) ratio of greater than 5 can be thought of as a one-dimensional (1-D) scanning x-ray tube due to its limited scanning range in the X-direction.

X-rays generated by the x-ray source 3 pass through the object 2 and are captured by an x-ray image sensor 5. The x-ray image sensor 5 comprises an array of x-ray detectors, as indicated by the shading of the upper surface 6 of the image sensor 5. Each detector of the image sensor 5 produces an electrical signal that is proportional to the amount of x-ray energy that impinges on it during the exposure time. The electrical signals preferably are converted (not shown) into digital signals that are suitable for processing by the processor 7, although this is not necessary. The electrical signals could instead be analog signals and the processing circuitry could be configured to process the analog signals. A piece of X-ray sensitive film could alternatively be used as the x-ray image sensor 5.

To accomplish the objectives of the present invention, preferably a processor 7 controls a source controller 8, which causes the x-ray source 3 to be appropriately addressed. To this end, the processor 7 performs at least two algorithms. The first of these algorithms determines the manner in which the point source is moved to ensure that the image of the object 2 on the image sensor 5 is effectively stationary. The second algorithm is an inspection algorithm that processes data corresponding to signals produced by the x-ray detectors of the image sensor 5 to inspect the object 2. These algorithms may be distinct from each other or may be contained in a single program that has multiple corresponding routines. For purposes of simplifying the discussion and for ease of illustration, a single processor 7 is shown for performing these algorithms. However, persons skilled in the art will understand that any one or more of these algorithms could be off-loaded onto one or more other processors (not shown). Moreover, the first algorithm need only be performed once unless the motion of the object changes.

The first algorithm receives data from the object motion control unit (not shown) or from the production line conveyor system (not shown) concerning the direction and velocity of the motion of the object, as well as the distance of the object 2 from the illumination source 3 and from the image sensor 5. All of this information is readily available or can easily be obtained. The first algorithm processes this data and determines when a given position on the x-ray scanning tube 3 should be addressed to ensure that the motion of the point source moves in the Y-direction with a velocity that corresponds to the velocity in the Y-direction of the object 2. The manner in which the relationship between the velocity of the point source and velocity of the object is determined will be discussed below with reference to FIGS. 2A and 2B. The processor 7 outputs the point source addresses to the source controller 8, which then causes the appropriate point source position to be addressed on the scanning x-ray tube 3. The processor 7 and the source controller 8 together form processing circuitry for positioning the point source at the appropriate position on the scanning x-ray tube 3.

It should be noted that it is not necessary for either or both of the processor 7 and source controller 8 to be used to control the position of the point source in the illumination source 3. Instead, the illumination source 3 could have its own functionality that enables it to move the point source in a manner that ensures that the image of the object 2 remains stationary on the image sensor 5. As will be recognized by those skilled in the art, a number of ways, both digital and analog, exist to cause the appropriate motion to be imparted to the point source. In accordance with the preferred embodiment, the processor 7 is used to generate the appropriate addresses of the point source. The source controller 8 receives the addresses from the processor 7 and causes the corresponding positions of the point source in the illumination source to be addressed at the appropriate times. In the interest of brevity, the task of addressing the positions will be discussed only with reference to the preferred embodiment.

In accordance with the preferred embodiment, the second algorithm performed by the processor 7 is an inspection algorithm. When executing this algorithm, the processor 7 processes electrical signals that correspond to the electrical signals output from the image sensor 5 in response to x-rays passing through the object 2 and impinging on the image sensor 5. The algorithm combines and processes the electrical signals in a manner to provide useful information about the object 2, as is typical for automated inspection systems. The manner in which x-ray imaging systems perform various types of inspection algorithms in order to examine an object are known. Any of these types of known algorithms as well as any algorithms developed in the future for this purpose are suitable for use with the present invention.

Generally, for each region of the object 2 to be inspected, the image sensor 5 is exposed for a period of time during which the point source of illumination is moved in a manner such that an image of substantially the same region of the object 2 is projected onto the same detector of the image sensor 5. This is illustrated by the portions of the cone-shaped x-ray beams 9A and 9B, which pass through substantially the same region of the object 2 as it moves and impinge on a detector 11 of the image sensor 5. As the object moves in the Y-direction from positions 2A to 2B, at each of the positions Y1 and Y2 of the point source of the scanning x-ray tube 3, the portions of the beams 9A and 9B projected from positions Y1 and Y2, respectively, pass through substantially the same region of the object 2 and impinge on the same detector 11 of the image sensor 5. Thus, the image of the object 2 projected onto the image sensor 5 remains effectively stationary on the image sensor 5. The continuum of positions on the scanning x-ray tube 3 of the point source from which x-rays are projected ensures that the x-rays that pass through the object from each position of the point source of illumination will cause overlapping images of that region to be projected onto the same region of image sensor 5.

If the object 2 had no thickness whatsoever, then for a given region, identical views of that region of the object 2 would be captured at both of the positions 2A and 2B. However, because any object will have some thickness, then for any given region, a slightly different view of the region of the object 2 will be captured at each position. Specifically, the location at which the projected x-rays intersect the bottom side of the object 2 will change slightly, as described below in more detail with reference to FIGS. 2A and 2B. Consequently, the composite image for any given region will be made up of the combination of the slightly different, but mostly overlapping, views captured at each Y position. For this reason, the composite image for any given region will contain images of the region in at least both the Y and Z (thickness) dimensions taken from different projection angles of the region, which is advantageous. Complementary information can be obtained and combined using tomographic or tomosynthesis techniques, or the like. Furthermore, because the views are substantially identical at each position of the point source for any given region, blurring is minimized.

FIGS. 2A and 2B illustrate the manner in which substantially the same, but non-identical, views of a particular region of the object are captured as the position of the point source moves synchronously with the position of the object. In FIG. 2A, the point source 12 at position A projects x-rays through an object 19 and causes an image of region 14 of the object 19 to be projected onto detector 15 of x-ray image sensor 5 (FIG. 1). Because the image sensor 5 remains stationary and because the object 19 has some thickness (even though it would generally be categorized as a "flat object"), even though the position of the point source is synchronized with the motion of the object 19, a slightly different region 14' (FIG. 2B) of the object 19 that overlaps the region 14 (FIG. 2A) of the object 19 is projected onto detector 15 of the image sensor 5. As stated above, the projected x-rays will intersect the bottom side of the object 19 at slightly different locations, but the imaged regions 14 and 14' of the object 19 almost entirely overlap. Also, as the thickness of the object 19 decreases, the amount of overlap of the regions 14 and 14' increases.

A comparison of FIG. 2A with FIG. 2B shows a slight difference between the shapes of the imaged regions 14 and 14' of object 19. In FIG. 2B, the position of the x-ray 13 in reference to the bump 21 on the surface of the object 19 indicates that the object 19 has moved in the Y-direction. The difference between the outline of the x-ray 13 and the x-ray 17 at position B illustrates the slight difference between the locations at which x-rays 13 and 17 intersect the bottom of regions 14 and 14', respectively, and also shows the overlap of the regions 14 and 14' of the object 19. This allows slightly different views of substantially the same region of the imaged object at slightly different projection view angles to be captured with minimal blurring.

The position of the point source 12 in FIG. 2A corresponds to the position of the point source at the beginning of exposure. The position of the point source 18 in FIG. 2B corresponds to the point source position at the end of the exposure time, $\Delta t$, which is known. When the positions of the point source and of the object 19 move at velocities $V_S$ and $V_O$, respectively, a region 14 of the object 19 that is slightly different from the region 14 of the object 19 is projected onto the image sensor 5. The distance between the positions of the point source is equal to the point source velocity $V_S*\Delta t$. The velocity of the object $V_O$ is known, as are the distances between the image sensor 5 and the object 19, $r_{OD}$, and the distance between the source and the object, $r_{SO}$. From the distances $r_{OD}$ and $r_{SO}$, the value K can be calculated as follows: $(r_{OD}+r_{SO})/r_{OD}=K$. Since the velocity of the object 19 is known, the velocity $V_S$ at which the point source should move continuously to ensure that the image on the image sensor 5 remains stationary can be calculated as follows: $V_S=V_O*K$.

It should be noted that for the velocities as defined in the FIGS. 2A and 2B, the top surface of the object 19 projects identically for both point source position A and point source position B. In this manner, if the point source position is moved continuously during the exposure, the exposure accumulates a projected view on the detector 15 of the image sensor 5 of a region of the object 19 that is represented by either 14 or 14' to a predictable degree of accuracy, as all intermediate positions will largely overlap. If the position of the point source were to remain stationary at position A, the projected region of the object at the end of the exposure would be completely different from the projected region of the object at the beginning of the exposure, and their would be no overlap, thereby causing substantial blurring.

Figure 3:
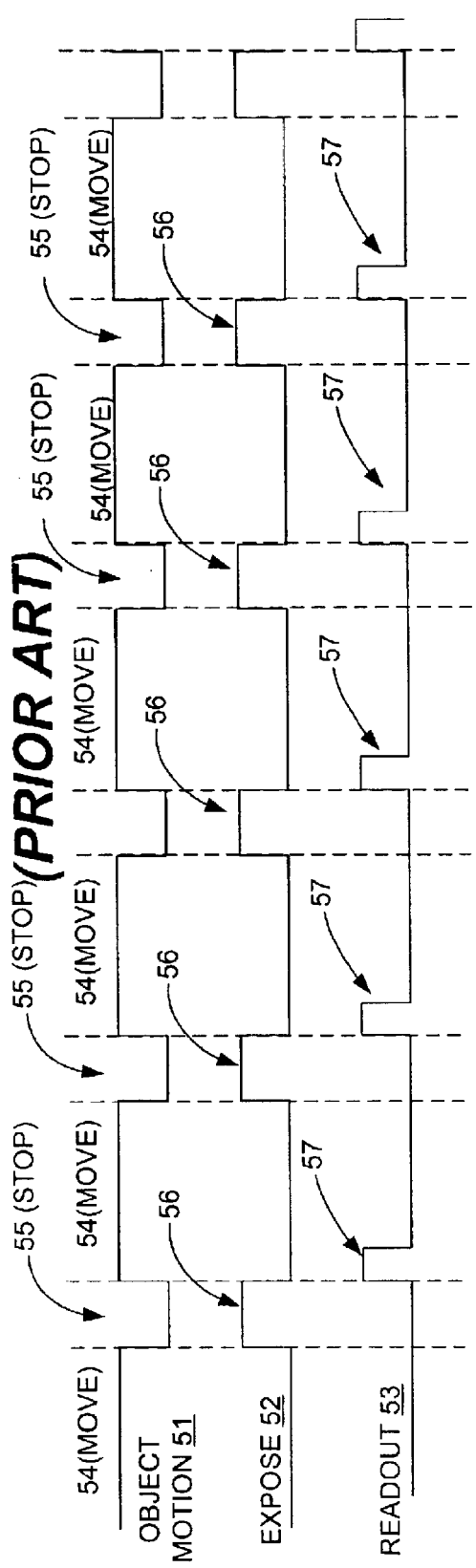
FIG. 3 is a timing diagram illustrating a known imaging technique, which requires that the motion of the object be halted and that the object be allowed to settle each time the object is to be illuminated and corresponding signals from the detector are to be read out from the detector.
Figure 4:
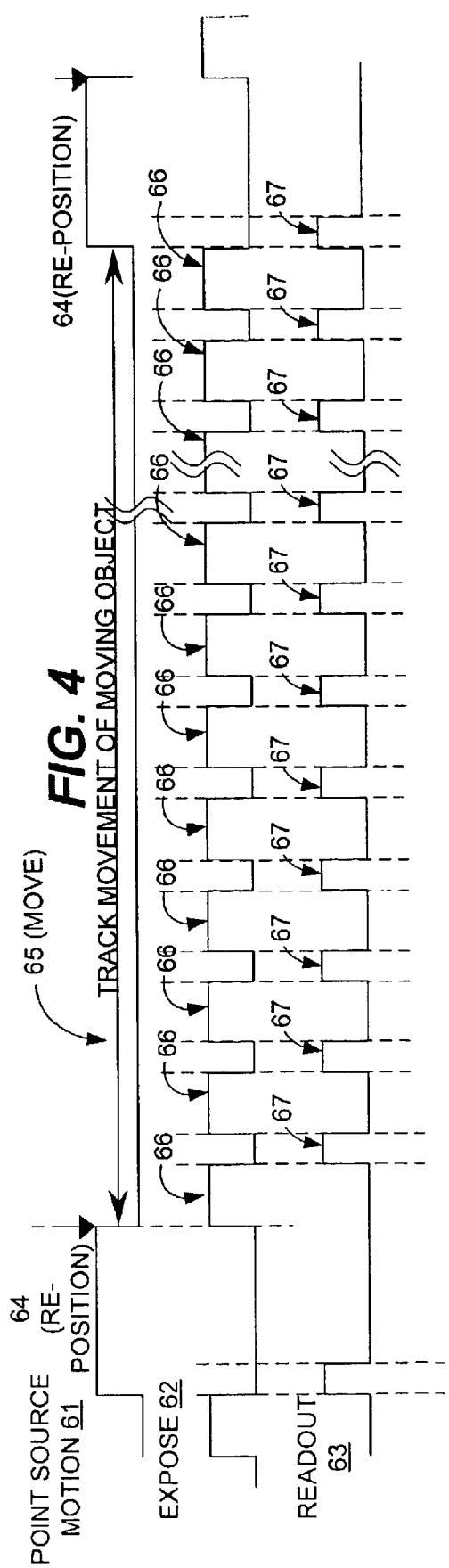
FIG. 4 is a timing diagram illustrating the imaging technique of the present invention in accordance with the multiple-pass imaging embodiment of FIG. 4.

FIG. 3 is a timing diagram of the known technique for imaging an object wherein the object is stopped and allowed to settle each time it is to be exposed and sampled. FIG. 4 is a timing diagram illustrating an example embodiment of the sampling technique of the present invention wherein exposure and sampling occur for a substantial period of time while the object is in continuous motion. Such a continuous motion period will be referred to hereinafter as a "pass", which corresponds to imaging a region of an object until it is time to image a different region of the object. In accordance with this embodiment of the present invention, the motion of the object is only stopped long enough for the object to be repositioned in order to image the new region of the object. No imaging of the object is performed while the object is being repositioned because it is desirable to move the object very rapidly to the start of a new pass.

In FIG. 3, which corresponds to the known technique, the top waveform 51 represents the motion of the object. When the waveform 51 is high as indicated by the portions of the waveform labeled with reference numeral 54, the object being imaged is moving rapidly and then settling to a new region of the object to be imaged. When the waveform 51 is low, as indicated by the portions of waveform 51 labeled with reference numeral 55, the motion of the object has been halted and the object has settled to sufficient precision to begin imaging. The waveform 52 represents the period of exposure of the object by an illumination source after the motion of the object has been halted and the object has settled. It can be seen that when the motion waveform 51 is high, as indicated by reference numeral 54, the exposure waveform 52 is low, and vice versa. Waveform 53 represents the period after exposure when the value generated by an image sensor is read out from the image sensor, i.e., the image sensor output is sampled. A readout period, which is represented by the reference numeral 57, occurs immediately after the exposure period 56. The object motion resumes after the exposure period 56.

In FIG. 4, which corresponds to an embodiment of the present invention, many exposures and readouts occur during the motion of the object during each pass. The top waveform 61 represents the motion of the point source in the Y-direction. When the waveform 61 is high, as indicated by reference numeral 64, the point source is moving at a very high speed to access a region of the object that needs to be imaged. When the waveform 61 is low, as indicated by reference numeral 65, the motion of the point source has been reduced to the velocity that ensures that the image on the image sensor 5 remains effectively stationary. The velocity of the object in the Y-direction is preferably constant, but is not necessarily so. The velocity of the object need only be sufficiently well known to be directly tracked in the manner discussed above with reference to FIGS. 2A and 2B. The waveform 62 represents the period of exposure of the object by the illumination source 3. When waveform 62 is high, as indicated by reference numeral 66, the object is being exposed. Waveform 63 represents the period after exposure when the value generated by an image sensor is read out from the image sensor 5. When waveform 63 is high, as indicated by reference numeral 67, the values generated by the image sensor 5 are read out from the image sensor 5.

A comparison of exposure waveform 52 of FIG. 3 with exposure waveform 62 of FIG. 4 shows that the object can be exposed many more times in accordance with this embodiment of the present invention than with the known technique. A comparison of waveform 63 of FIG. 4 with waveform 53 of FIG. 3 shows that this embodiment of the present invention enables the number of times that the image sensor 5 is read to be drastically increased. The frequency of the exposures and readouts shown in FIG. 4 prevent or minimize blurring of the captured images. The infrequent stopping of the motion of the object increases the throughput of the imaging system.

It should also be noted that the timing diagrams of FIGS. 3 and 4 are not drawn to scale with respect to timing, but are drawn simply to illustrate the differences between the stop-and-go imaging technique of the prior art and the virtually continuous imaging technique of the present invention. It is the elimination of the stop periods in the acquisition sequence that is the source of the primary throughput gains of the present invention. It also is not necessary that the point source have periods of high-speed motion during imaging. If the distance over which the point source can be moved is sufficient to image the entire object in a single pass, then no repositioning of the point source (the periods when waveform 61 is high) would be required.

With current source and image sensor technologies, it is not unreasonable to obtain more than 1000 views during a single pass. The number of views obtained is limited only by the illumination brightness of the source during exposure, the image sensor sensitivity and the image sensor readout speed. Obtaining unique views implies additional constraints such as the maximum velocity that can be tracked with tolerable blur, the thickness of the object to be imaged, the size of the detector, and the like. Conversely, if throughput requirements provide sufficient financial incentive, multiple imaging engines could be positioned within a single tool and an entire object wider than the imaging engine could be imaged in a single passage of the object through such a system. Technology today should allow illumination brightness and image sensor sensitivity to be driven to the physical limits of source target melting and Poisson limited photon detection, respectively, for x-ray imaging.

It should be noted that the above-described embodiments of the present invention are only examples of possible implementations. Those skilled in the art will understand from the present disclosure that many variations and modifications may be made to the embodiments described herein without departing from the scope of the present invention. All such modifications and variations are within the scope of the present invention.

What is claimed is:

1. An imaging system for capturing images of a moving object, the system comprising:
   an illumination source capable of projecting illumination from a plurality of different positions relative to an imaging plane, each of said plurality of positions acting as a point source of illumination when illumination is projected therefrom, the position from which illumination is projected at any given time being controllable in such a manner that the position from which illumination is projected onto the moving object is changed as the object moves so that the position of an image of the moving object projected onto said imaging plane remains substantially stationary; and
   a image sensor located in said imaging plane, the image sensor receiving illumination projected from any one of said plurality of different positions that passes through the moving object, the image sensor producing electrical signals in response to illumination received thereby from which an image of at least a portion of the moving object can be captured with minimal blurring of the image.

2. The system of claim 1, further comprising processing circuitry for controlling the position from which illumination is projected from the illumination source to ensure that the position from which illumination is projected changes synchronously with the motion of the object.

3. The system of claim 2, wherein the processing circuitry includes a processor that executes a source control algorithm that processes the information received relating to the motion of the moving object to determine the positions from which the illumination beams should be projected to ensure that the position of the projected beam of illumination remains substantially constant with respect to the position of the moving object.

4. The system of claim 1, wherein the illumination source is a scanning x-ray tube comprising a plurality of addressable positions from which illumination can be projected, wherein when a given position of the scanning x-ray tube is addressed, x-rays are projected from that given position onto the object, and wherein the electrical signals produced by the image sensor relate to an amount of x-ray energy that passes through the object and impinges on the image sensor.

5. The system of claim 1, wherein the system is used to generate substantially blur-free images of objects as the objects move along a production line, and wherein the processing circuitry includes a processor that executes an inspection algorithm that analyzes the captured images to determine whether or not the objects have defects.

6. A method for capturing images of a moving object, the method comprising:
   projecting illumination from one of a plurality of different positions relative to an imaging plane onto the moving object;
   controlling the position from which the illumination is projected onto the moving object such that a position of an image of the moving object projected onto said imaging plane remains substantially stationary;
   detecting illumination at the imaging plane to generate electrical signals from which an image of at least a portion of the moving object can be constructed with minimal blurring.

7. The method of claim 6, wherein:
   the positions from which the illumination is projected are addressable; and
   the position from which illumination is projected functions as a point source of illumination; and
   the position from which the illumination is projected is determined by addressing one the different positions.

8. The method of claim 7, wherein the illumination is projected from a scanning x-ray tube and wherein the illumination projected from the illumination source is x-ray radiation, and wherein the electrical signals produced by the image sensor relate to an amount of x-ray energy that passes through the object and impinges on the image sensor.

9. The method of claim 8, further comprising processing the electrical signals produced by the image sensor corresponding to multiple images of the object in accordance with an image processing algorithm to produce an image of the object with minimal blur.

10. The method of claim 9, further comprising processing the electrical signals generated by the image sensor in accordance with an inspection algorithm that analyzes the images to determine whether or not the object conforms to a prescribed set of specifications.

11. The method of claim 9, wherein controlling the position from which the illumination is projected includes executing a source control algorithm in response to information relating to the motion of the moving object to determine the positions from which the illumination should be projected to ensure that the image projected onto the image sensor remains effectively stationary.

12. A computer program for capturing images of a moving object with minimal blurring, the computer program being embodied on a computer-readable medium, the program comprising:
   a first routine for controlling a position from which illumination is projected from an illumination source relative to an imaging plane onto a moving object in such a manner that the position of the image of the moving object projected onto said imaging plane remains substantially stationary, wherein the illumination is projected onto the object while the object is moving and wherein projected illumination that passes through the object is detected by a image sensor positioned in the imaging plane, and wherein the image sensor converts the detected illumination into electrical signals; and
   a second routine for processing data corresponding to the electrical signals to construct an image of at least a portion of the object with minimal blurring.

* * * * *